Figure 1:
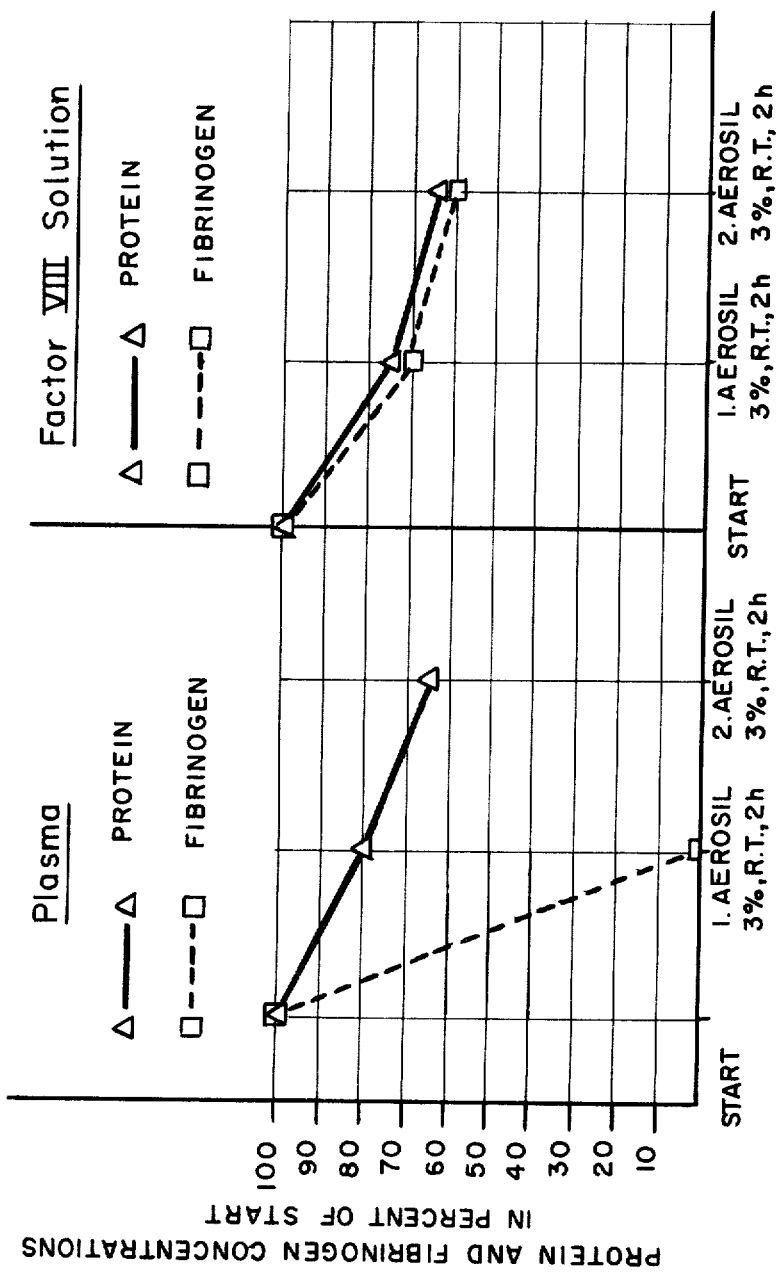

United States Patent [19]

Kotitschke et al.

[11] 4,370,264

[45] Jan. 25, 1983

[54] METHOD FOR THE COLD STERILIZATION OF PREPARATIONS CONTAINING BLOOD COAGULATION FACTOR VIII

[75] Inventors: Ronald Kotitschke; Wolfgang Stephan, both of Dreieich, Fed. Rep. of Germany

[73] Assignee: Biotest-Serum-Institut GmbH, Frankfurt am Main, Fed. Rep. of Germany

[21] Appl. No.: 300,074

[22] Filed: Sep. 8, 1981

[30] Foreign Application Priority Data

Sep. 10, 1980 [DE] Fed. Rep. of Germany ....... 3033932

[51] Int. Cl.³ .............................................. C07G 7/00
[52] U.S. Cl. ................ 260/112 B; 424/101
[58] Field of Search ..................... 260/112 B; 424/101

[56] References Cited

U.S. PATENT DOCUMENTS

| 3,717,708 | 2/1973 | Wada et al. ................. 260/112 B X |
| 4,069,216 | 1/1978 | Shanbrom ..................... 260/112 B |
| 4,081,431 | 3/1978 | Stephan et al. ................ 260/112 B |
| 4,170,590 | 10/1979 | Stephan et al. ............... 260/112 B |
| 4,251,437 | 2/1981 | Rasmussen et al. ............ 260/112 B |
| 4,272,523 | 6/1981 | Kotitschke et al. ......... 260/112 B X |
| 4,305,870 | 12/1981 | Liu et al. ........................ 260/112 B |
| 4,318,902 | 3/1982 | Stephan .............................. 424/85 |

OTHER PUBLICATIONS

Pharmacology, vol. 2, (1969), pp. 1–8, Doleschel et al.
Vox Sanguinis, vol. 8 (1963), pp. 105–109, S. Gouris et al.
Bibl. Haematol., vol. 7 (1958), pp. 225–230, LoGrippo et al.

*Primary Examiner*—Howard E. Schain
*Attorney, Agent, or Firm*—Sprung, Horn, Kramer & Woods

[57] ABSTRACT

A process for the cold sterilization of a preparation containing blood coagulation factor VIII, comprising
(A) contacting a protein solution containing factor VIII with a physiologically compatible, non-ionogenic tenside, and then subjecting the solution to
(B) irradiation with ultraviolet light,
(C) treatment with beta-propiolactone, and
(D) to an adsorption treatment with colloidal silica, steps B-C-D being performed in the sequence B-C-D, B-D-C, D-C-B or D-B-C.

6 Claims, 3 Drawing Figures

Adsorptive Treatment of Plasma and a Factor VIII Solution with Colloidal Silicic Acid Adsorption Adsorbtive Treatment of Plasma and a
Factor VIII Solution with Colloidal Silicic Acid Dependence of Factor VIII Activity on the Concentration of β-Propiolactone in Purified Factor VIII Solutions

METHOD FOR THE COLD STERILIZATION OF PREPARATIONS CONTAINING BLOOD COAGULATION FACTOR VIII

BACKGROUND

The invention relates to a method for the cold sterilization of preparations containing blood coagulation factor VIII.

Congenital or acquired blood coagulation disorders attributable to a deficiency or insufficiency of plasmatic coagulation factors can be treated with preparations containing these factors in a concentrated form. These concentrates include fractions prepared from blood plasma. The fractions most commonly used at this time are Cohn fraction I obtained by alcohol fractionation according to Cohn (J. Am. Chem. Soc., vol. 72 (1950), p. 465), a cryoprecipitate obtained by cold precipitation, a fraction containing factor VIII (antihemophilic globulin=AHG), and an AHG concentrate containing antihemophilic globulin and the prothrombin complex, i.e., factors II, VII, IX and X (PPSB). Will all of these preparations there exists the risk of transmitting hepatitis.

The radioimmune assay for hepatitis B surface antigen (HBsAg) is 100 to 1000 times too insensitive, so that a high percentage even of HBsAg-negative blood products, especially AHG and PPSB preparations is infectious and capable of transmitting hepatitis B (cf. J. H. Hoofnagle et al., "The prevalence of Hepatitis B Surface Antigen in Commercially Prepared Plasma Products", J. Lab. Clin. Med., vol. 88 (1976), pp. 102 to 112, and R. J. Wyke et al., "Transmission of Non A-Non B Hepatitis to Chimpanzees by Factor IX Concentrates after Fatal Complications in Patients with Chronic Liver Disease", The Lancet 1 (1979), no. 8115, pp. 520 to 524).

Since it is not possible by diagnostic measures to obtain hepatitis-safe blood products from plasma pools, the sterilization of blood and blood components acquires central importance. Human albumin, for example, is made hepatitis-safe by pasteurization, i.e., by heating for 10 hours at 60° C. Coagulation factors, however, cannot be pasteurized, because they are destroyed even by one hour of heating at 60° C. Therefore, a method of sterilization would have to be developed which would operate at low temperatures rather than high. Such a method was proposed by LoGrippo (cf. G. A. LoGrippo et al., "Chemical Sterilization of Whole Blood and Plasma with Beta-Propiolactone", Hepatitis Frontiers, Henry Ford Hospital, Int. Symposium 1956, Little, Brown and Co., Boston, Mass. (1957), pp. 371 to 385, and G. A. LoGrippo et al., "Chemical and Combined Methods for Plasma Sterilization", Bibl. Haematol., vol. 7 (1958), pp. 225 to 230). This method consisted in the treatment of human plasma with beta-propiolactone, which could be combined with ultraviolet irradiation. It was also called "cold sterilization" because it was performed at temperatures below 37° C.

The application of the sterilization conditions given by LoGrippo, however, results in high losses of the factor VIII activity in plasma, as shown in the following Table I°.

TABLE I

The effect of LoGrippo's sterilization conditions on factor VIII activity in plasma.

| | Factor VIII in % of normal |
|---|---|
| Fresh citrate plasma | 100 |
| After treatment with beta-propiolactone (0.3%) | 55 |
| After ultraviolet radiation (2 mW/cm$^2$/min) | 30 |

Only inadequate yields of cryoprecipitate can be obtained from plasma treated with beta-propiolactone and ultraviolet. The combination of beta-propiolactone with ultraviolet treatment of extracts of cryoprecipitate is possible, but under the conditions given by LoGrippo it results in great losses of the Factor VIII activity.

J. T. Sgouris et al., "Stability of Factor I (Fibrinogen) and Factor VIII (Antihemophilic Globulin) to Beta-Propiolactone", Vox Sang., vol. 8 (1963), pp. 105 to 108, W. Doleschel et al., "The Influence of Beta-Propiolactone on the Coagulability of Human Fibrinogen", Pharmacology, vol. 2 (1969), pp. 1 to 8; and H. Brunner et al., "Experimentelle Fibrinogenopathie nach Reaktion von humanem Fibrinogen mit β-Propiolactone: Antithrombinaktivität, Wirkung auf die Plättchenaggregation und Funktion auf die Fibrinverfestigungsphase", Verhandlungen der Deutschen Gesellschaft für Innere Medizin, vol. 79 (1973), pp. 1130 to 1134, attempted to use beta-propiolactone for the sterilization of coagulation factors, especially protein fractions containing factor VIII and fibrinogen.

It was found, however, as a result of this work that the method described by LoGrippo for the sterilization of plasma or serum with beta-propiolactone and ultraviolet radiation is not appropriate for the production of fibrinogen or of preparations containing factor VIII, since these proteins either suffer excessive activity losses or the beta-propiolactone concentration given by LoGrippo has to be reduced to such an extent that a sufficient viricidal action is not realized.

In the production of vaccines it is common to combine different inactivation methods for the inactivation of viruses, for the purpose of eliminating "resistant fractions" which might be resistant to one particular method of inactivation, but which are inactivated by a second or third treatment whose inactivation mechanism is different from that of the first treatment.

THE INVENTION

It is the object of the invention to cold-sterilize preparations which contain blood coagulation factor VIII, e.g., a fraction obtained by extraction from cryoprecipitate and containing factor VIII or a Cohn fraction I which must be considered as infectious, doing so by means of a plurality of methods of chemical and/or physical virus inactivation and/or virus adsorption, such that on the one hand any infectivity will be inactivated, but on the other hand the biological activity of the factor VIII protein will be impaired to the least possible extent.

This object is achieved in accordance with the invention by the fact that a protein solution containing factor VIII A—is treated with a physiologically compatible, non-ionogenic tenside, B—is subjected to ultraviolet irradiation, C—is treated with beta-propiolactone, and D—is subjected to an adsorption treatment with colloidal silica, steps B, C and D also being performable in the order B, D, C or D, C, B or D, B, C.

The concept of sterility is not clearly defined. It is therefore always necessary to state the method by which sterility is achieved. The method of the invention is a method for the achievement of sterility.

In the method of the invention, a protein solution containing factor VIII can be used as starting material which is obtained by known methods by isolation of cryoprecipitate (cold precipitation) from a blood plasma stabilized with a blood stabilizer (cf. J. G. Pool et al., Federation Proc., vol. 24 (1965), p. 512, abstract 2122) and processed by known methods (cf., for example, A. J. Johnson et al., "Preparation of and Clinical Experience with Antihemophilic Factor Concentrates", Thrombos. Diethes. Haemorrh., Suppl. 35 (1969), pp. 49 to 59; J. Newman et al., "Methods for the Production of Clinically Effective Intermediate- and High-Purity Factor VIII Concentrates", Brit. J. of Haematology, vol. 21 (1971), pp. 1 to 20; and R. H. Wagner et al., "Purification of Antihemophilic Factor (Factor VIII) by Amino Acid Precipitation", Thrombos. Diathes. Haemorrh., vol. 11 (1964), pp. 64 to 74). A Cohn fraction I can also be used.

The solutions containing factor VIII which are obtained in this manner often contain, in addition to concentrated factor VIII, fibrinogen in highly concentrated form.

The virus inactivation or elimination treatment in accordance with the invention consists in the combination of four successive measures, none of which has any great adverse effect on the factor VIII activity.

The effect of the individual measures on the factor VIII activity will be further explained below.

Figure 2:
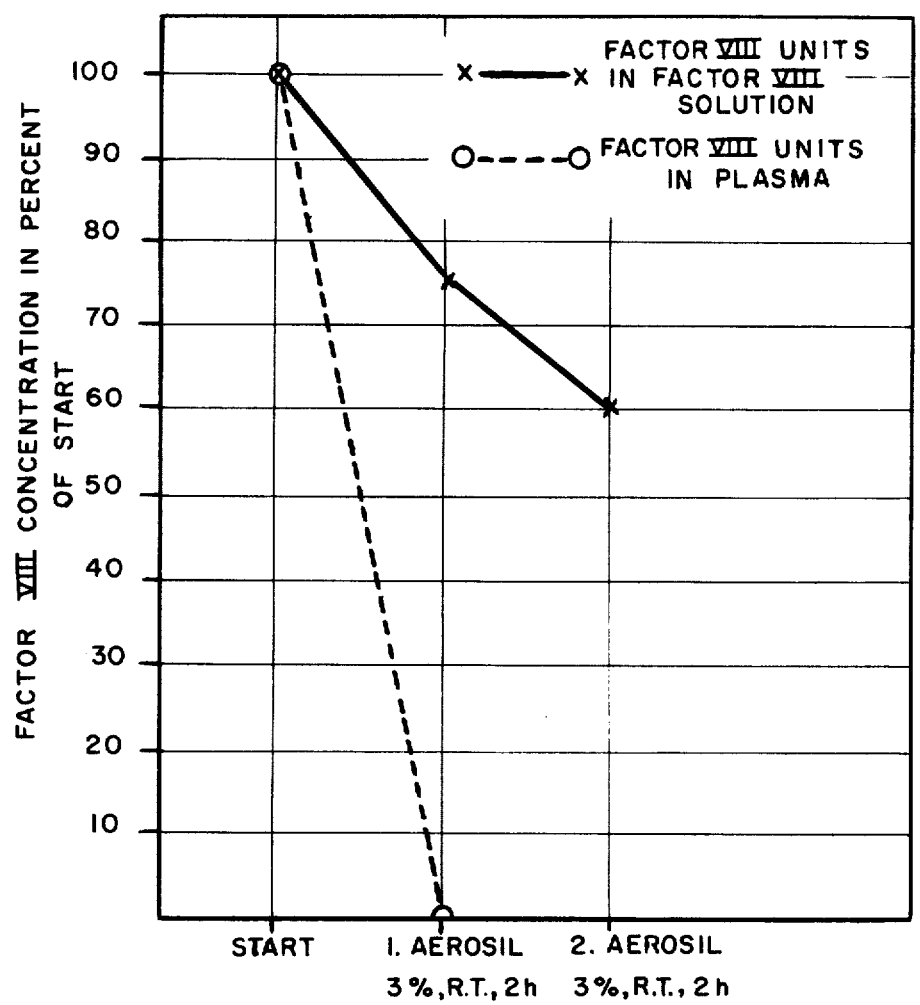
Figure 3:
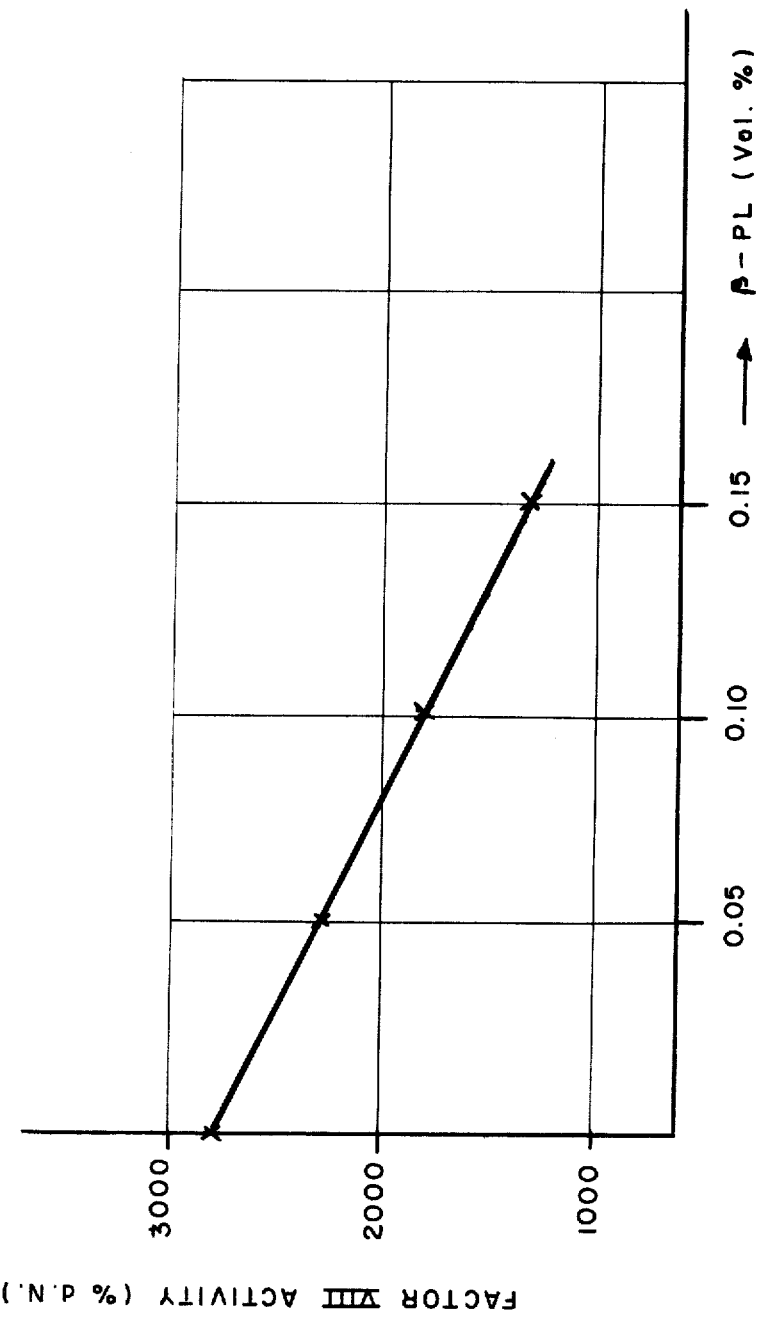

The invention will be further described with reference to the accompanying drawings wherein:

FIGS. 1 and 2 are plots of protein and fibrinogen concentrations against silica for both plasma and a factor VIII solution; and FIG. 3 is a plot of factor VIII B-propiolactone treatment.

TENSIDE TREATMENT

To a factor VIII fraction obtained by extraction from cryoprecipitate or some other protein solution containing factor VIII a physiologically compatible, non-ionogenic tenside in a concentration of 1.0 to 5.0% is added, and the mixture is treated at room temperature. Sorbitan fatty acid esters and polyoxyethylene derivatives thereof can be used, for example, as tensides.

It is preferable to use sorbitan mono- and tri-fatty acid esters based on lauric, palmitinic, stearic and oleic acid, as well as the corresponding polyoxyethylene derivatives (the commercial names of these products are Span ® and TWEEN ®). The good water solubility of the polyoxyethylene derivatives and the good tolerability of these sorbitan fatty acid esters generally (LD$_{50}$ greater than 37 g/kg in rats) favor the preferred use of these tensides in the process of the invention.

Any influence of these tensides on factor VIII activity, when they are used in concentrations up to a total of 3% in the solution being treated, is undetectable, as is shown in Table II.

TABLE II

| | Tenside concentration, % | | |
|---|---|---|---|
| | Sorbitan oleate (Span$^R$85) | Polyoxyethylene-20-sorbitan monooleate (TWEEN$^R$ 80) | Factor VIII (% of normal) |
| Starting mixture | 0 | 0 | 500 |
| 1 h, room temperature | 1 | 1 | 500 |
| 1 h, room temperature | 2 | 2 | 500 |
| 1 h, room temperature | 3 | 3 | 450 |

Relationship between factor VIII activity and tenside concentration.

Adsorption Treatment with Colloidal Silica

When the attempt was made to use colloidal silica for the adsorption of any viruses that might be present in the factor VIII solution, it was surprisingly found that the factor VIII activity and the fibrinogen were largely preserved in the factor VIII solution.

That viruses can be bound to colloidal silica is known (German Pat. No. 1,617,319) but it is also known that colloidal silica is used for the adsorption of fibrinogen and unstable proteins (German Offenlegungsschrift No. 2,902,158).

In the treatment for the adsorption of a factor VIII concentrate solution onto silica it was surprising that neither fibrinogen nor factor VIII was adsorbed onto the silica from the factor VIII concentrate solution. This finding was directly contrary to the known findings to the effect that factor VIII and fibrinogen are completely adsorbed by colloidal silica. The results of experiments to this effect are represented in FIGS. 1 and 2. The losses occurring in FIG. 2 are explained by the loss of liquid during the adsorption. The following Table III shows that the activity of factor VIII and the fibrinogen concentration of the solution containing factor VIII are virtually identical before and after adsorption with colloidal silica°.

TABLE III

How the Factor VIII Activity and Fibrinogen Concentration Are Affected by Adsorption with Colloidal Silica.

| | Volume (ml) | Factor VIII (% of normal) | Fibrinogen (mg %) |
|---|---|---|---|
| Starting mixture | 500 | 3000 | 1950 |
| After adsorption with colloidal silica (3%, 2 h, room temperature) | 360 | 3000 | 1850 |

The colloidal silica used for the adsorption treatment should preferably have a specific surface area of 50 to 400 square meters and be used in a concentration of 1 to 3 grams per gram of protein. The colloidal silica can be, for example, a commercial product sold under the trademark "Aerosil".

The adsorption with colloidal silica can be repeated and the adsorption temperature can even be raised to 45° C. without producing any substantial difference from the results obtained at room temperature.

Ultraviolet Irradiation

The ultraviolet irradiation of the factor VIII solution results in an activity loss of about 20%. In comparison, the activity loss of factor VIII in the combination of plasma proteins after treatment with beta-propiolactone in the concentrations proposed by LoGrippo amounted to nearly 50%, as already indicated in Table I.

Treatment with Beta-Propiolactone and Ultraviolet Irradiation

The preservation of the factor VIII activity of solutions containing factor VIII can be achieved only by departing from the conditions given by LoGrippo. The relationship between the factor VIII activity and various beta-propiolactone concentrations is represented in FIG. 3. At a beta-propiolactone concentration of 0.05%, the activity loss of a solution containing factor VIII with protein concentrations of 2 to 5 g/100 ml is approximately 20%. In the process of the invention, the concentration of the beta-propiolactone is to amount to from 0.012 to 0.067 grams per gram of protein.

The subsequent ultraviolet irradiation (LoGrippo's specification, i.e., 2 mWatt/cm$^2$/min) again causes an activity loss of about 20%, as indicated in the following Table IV°.

TABLE IV

Effect of Treatment with Beta-Propiolactone and Ultraviolet Light on the Factor VIII Activity of Solutions Containing Factor VIII.

|  | Factor VIII, % of normal | Remaining Factor VIII Activity, % |
|---|---|---|
| Starting solution | 2,800 | 100 |
| Beta-Propiolactone (0.05%) | 2,300 | 82 |
| Ultraviolet light (2 mW/cm$^2$/min) | 1,900 | 67 |

In order to test the entire cold sterilization process of the method with respect to the survival of hepatitis viruses, an HBsAg-positive plasma was added to a cryoprecipitate extract and the HBsAg concentration in the different fractions was then determined.

Table V shows the results obtained by the method of the invention, using the order A-B-C-D.

TABLE V

Quantitative HBsAg Distribution in the Processing of Cryoprecipitate to Which HBsAg Had Been Added.

| Virus Inactivation Steps | HBs Ag (ng/ml) |
|---|---|
| Starting mixture (cryoprecipitate) | 2,700 |
| 1. After tenside treatment | 170 |
| 2. After ultraviolet irradiation | 90 |
| 3. After beta-propiolactone treatment | 75 |
| 4. After adsorption treatment with colloidal silica | 0 |

Since in vitro tests with the hepatitis virus cannot be performed in the present-day state of the art, the coli phage proposed by LoGrippo as a suitable model for the hepatitis virus (G. A. LoGrippo: Investigation. Annals of the New York Acad. of Sciences, vol. 83 (1960), art. 4, pp. 578 to 595) was used in testing the effectiveness of the process.

For this purpose enough coli $T_2$ phages were added to a cryoprecipitate extract to achieve a starting concentration of $10^5$ viruses per milliliter.

Table VI shows the results obtained by performing the process in the order A-D-C-B.

TABLE VI

Phage Distribution in the Processing of Cryoprecipitate To Which Phages Had Been Added.

| Virus Inactivation Steps | Phage Concentration (viruses per ml) |
|---|---|
| Starting Mixture (cryoprecipitate) | $2 \times 10^5$ |
| 1. After tenside treatment | $10 \times 10^4$ |
| 2. After adsorption treatment with colloidal silica | $2 \times 10^5$ |
| 3. After treatment with beta-propiolactone | $2 \times 10^3$ |
| 4. After ultraviolet irradiation | 0 |

The increased concentration of the viruses from step 1 to step 2 is explained by a factor VIII concentration step which entails a volume reduction by one power of ten.

Preparation

Preparation of a Solution Containing Factor VIII

Nine parts of venous donor blood were added to one part of a 3.8% sodium citrate stabilizer solution. The blood was centrifuged as quickly as possible after it had been taken, and the erythrocytes suspended in physiological salt solution were reinfused into the donor. The plasma was frozen within no more than 48 hours at $-40°$ C.

The frozen plasma was thawed at $+4°$ C. and then centrifuged to separate the cryoprecipitate from the rest of the plasma, in a known manner.

The invention will be further described in the following illustrative examples.

EXAMPLE 1

Cold Sterilization of a Solution Containing Factor VIII, in the Order A-B-C-D

A. Treatment with physiologically compatible, non-ionogenic tenside.

A solution containing factor VIII in the form of cryoprecipitate obtained as described above was thawed at $+37°$ C. and, at room temperature, such an amount of 0.02 M tris buffer pH 6.5 (tris(hydroxymethyl)-aminomethane) was added that 100 ml of tris buffer was used per liter of starting plasma. Polyoxyethylene-20-sorbitan monooleate (TWEEN ® 80 of Atlas Chemie, Essen) was added to the mixture in a concentration of 3% by weight, then stirred for one hour at room temperature, and then centrifuged. The precipitate was discarded.

B. Ultraviolet Irradiation

The supernatant liquid obtained in step A was irradiated with ultraviolet light in an ultraviolet flow-through apparatus at 254 μm at 2 mW/cm$^2$/min. The irradiated solution was cooled to $+4°$ C. and then polyethylene glycol (with an average molecular weight of 4,000) was added to produce a PEG concentration of 1%, whereupon the mixture was stirred for 15 minutes and then centrifuged. The precipitate was discarded. The supernatant liquid was brought to a PEG concentration of 10% by the addition of polyethylene glycol 4000. The factor VIII precipitate thus formed was separated by centrifugation and dissolved in a buffer solution.

C. Treatment with Beta-Propiolactone

The factor VIII solution obtained in step B was treated with 0.05% (vol./vol.) of beta-propiolactone and maintained at room temperature for one hour at pH 6.5.

D. Adsorption Treatment with Colloidal Silica

The factor VIII solution treated with beta-propiolactone in step C was treated with 3 wt.-% of colloidal silica having a particle size of 8 nm and a specific surface area of 380 m²/g ("Aerosil 380" of Degussa) and stirred for 2 hours at room temperature. Then it was centrifuged and the precipitate was discarded.

The factor VIII solution was filtered sterile through sterile membrane filter disks, bottled and freeze-dried.

EXAMPLE 2

Cold Sterilization of a Solution Containing Factor VIII, in the Order A-D-C-B

A. Treatment with physiologically compatible, non-ionogenic tenside.

This treatment was performed by the method of Example 1 A.

B. Adsorption treatment with colloidal silica.

The factor VIII solution obtained in step A was stirred for 2 hours at 37° C. with 3 wt.-% of colloidal silica ("Aerosil 380") and then centrifuged and the precipitate was discarded.

C. Treatment with beta-propiolactone

Beta-propiolactone was added to the factor VIII solution obtained in step D to produce a concentration of 0.05% (vol./vol.) and the mixture was held for one hour at room temperature at pH 6.5.

D. Ultraviolet irradiation

The solution treated with beta-propiolactone in Step C was irradiated with ultraviolet light at 254 μm at 2 mW/cm²/min, using an ultraviolet flow-through irradiation apparatus.

The factor VIII solution thus irradiated was filtered sterile through sterile membrane filter disks, bottled, and freeze-dried.

It will be appreciated that the instant specification and examples are set forth by way of illustration and not limitation, and that various modifications and changes may be made without departing from the spirit and scope of the present invention.

We claim:

1. A process for the cold sterilization of a preparation containing blood coagulation factor VIII, comprising
    (A) contacting a protein solution containing factor VIII with a physiologically compatible, non-ionogenic tenside, and then subjecting the solution to
    (B) irradiation with ultraviolet light,
    (C) treatment with beta-propiolactone, and
    (D) to an adsorption treatment with colloidal silica, steps B-C-D being performed in the sequence B-C-D, B-D-C, D-C-B or D-B-C.

2. A process according to claim 1, wherein the treatments are carried out in the sequence B-C-D, and the solution after irradiation with ultraviolet light is fractionated before it is treated with beta-propiolactone.

3. A process according to claim 1, wherein the physiologically compatible non-iogenic tenside is a sorbitan fatty acid ester or polyoxyethylene derivative thereof in a concentration of about 1.0 to 5%.

4. A process according to claim 1, wherein the ultraviolet light is of an intensity of about 2 mWatt/cm²×min.

5. A process according to claim 1, wherein the beta-propiolactone is used in a concentration of about 0.012 to 0.067 g per g of protein.

6. A process according to claim 1, wherein the colloidal silica has a specific surface area of about 50 to 400 m² and is used in a concentration of about 1 to 3 g per g of protein.

* * * * *